United States Patent
Manca et al.

(10) Patent No.: US 7,605,256 B2
(45) Date of Patent: Oct. 20, 2009

(54) PROCESS FOR PREPARING SODIUM CEFOXITIN

(75) Inventors: Antonio Manca, Milan (IT); Riccardo Monguzzi, Dorio (IT); Maurizio Zenoni, Paullo (IT); Leonardo Marsili, Brescia (IT)

(73) Assignee: ACS DOBFAR S.p.A., Tribiano (IT)

( * ) Notice: Subject to any disclaimer, the term of this patent is extended or adjusted under 35 U.S.C. 154(b) by 485 days.

(21) Appl. No.: 11/425,560

(22) Filed: Jun. 21, 2006

(65) Prior Publication Data
US 2007/0027314 A1 Feb. 1, 2007

(30) Foreign Application Priority Data
Jul. 27, 2005 (IT) .................... MI2005A01451

(51) Int. Cl.
*C07D 501/04* (2006.01)
(52) U.S. Cl. ..................................... 540/221
(58) Field of Classification Search ................. 540/221
See application file for complete search history.

(56) References Cited

U.S. PATENT DOCUMENTS

2006/0252928 A1* 11/2006 Deshpande et al. ......... 540/222
2009/0093032 A1* 4/2009 Tagliani et al. .............. 435/118

FOREIGN PATENT DOCUMENTS

| IN | 2004CH00303 | * | 4/2004 |
| PL | 156026 | | 5/1989 |
| WO | WO 2004/083217 A1 | | 9/2004 |

OTHER PUBLICATIONS

PL156026 Translation (1989).*

* cited by examiner

*Primary Examiner*—Mark L Berch
(74) *Attorney, Agent, or Firm*—Oblon, Spivak, McClelland, Maier & Neustadt, L.L.P.

(57) ABSTRACT

Cefalotin is methoxylated in position $7\alpha$, desacetylated and then carbamoylated in position 3, to provide acid cefoxitin without any isolation of intermediate products. The acid cefoxitin is then transformed into the sodium salt by means of ion exchange resin.

6 Claims, No Drawings

PROCESS FOR PREPARING SODIUM CEFOXITIN

FIELD OF THE INVENTION

Cefoxitin is an injectable 7α-methoxy-cephalosporin of formula (I)

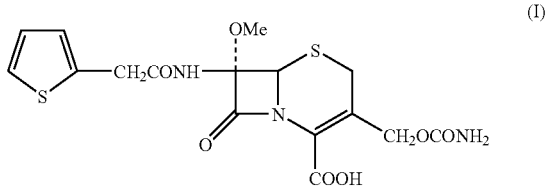

claimed for example in U.S. Pat. No. 4,297,488. The best cephalosporin for transformation into cefoxitin is cefalotin of formula (II)

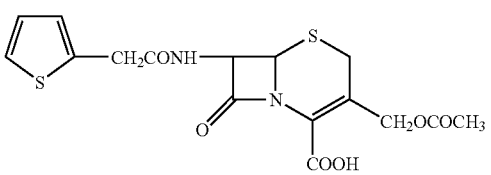

which is obtained by acylating 7-ACA with 2-thienyl-acetic acid. The cefoxitin molecule is characterised by the methoxyl in position 7α, by the carbamoyl-oxymethyl group in position 3 and by the 2-thienylacetamide group in position 7β.

DESCRIPTION OF RELATED ART

GB1350772 already claims a method for transforming the 3-hydroxymethyl group of 3-hydroxy-methyl-7-(2-thienylacetamide)-3-cefem-4-carboxylic acid, namely 3-desacetyl-cefalotin, of formula (III)

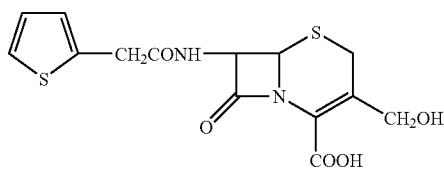

into the corresponding 3-carbamoyloxymethyl group, using isocyanates such as chlorosulphonylisocyanate. Another example is described in DOS 2264651 for the carbamoylation of 7α-methoxy-3-desacetyl-cerfalotin of formula (V)

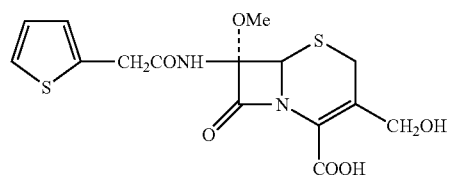

Hence it appears that the process commonly used for carbamoylation of 7α-methoxy-3-desacetyl-cerfalotin comprises the use of an isocyanate, and in particular chlorosulphonylisocyanate.

Numerous other processes exist for introducing the methoxyl in position 7α.

For example U.S. Pat. No. 3,994,885 and U.S. Pat. No. 4,044,000 describe a series of positive halogen donors including t-butyl-hypochlorite, N-chlorosuccinimide, N-chloroacetamide, N-haloamides and N-haloimides in general, chlorine, halohydantoins such as dibromohydantoin and N-halosulphonamides.

These positive halogen donors make it possible to halogenate the amide nitrogen of the thienylacetamide substituent in position 7β of the cephalosporin which, in the presence for example of sodium methylate, by way of a well known widely described elimination mechanism (dehydrohalogenation) followed by addition, leads to the stereoselective introduction of the methoxyl group to the carbon in position 7α of the cephalosporanic nucleus.

Other examples of methoxylation in position 7α using positive halogen donors are available in the cephalosporin chemical literature, however we consider that those cited are sufficient.

It is however apparent that the literature describes only processes in which the different process steps are quite distinct, requiring isolation of intermediates, with yield losses and longer unproductive times than those which the chemical process would require in itself.

As confirmation of the aforestated, EP 0204517A2 can be cited, which claims a process for preparing 7β-acylamino-3-hydroxymethyl-3-cefem-4-carboxylic acids useful as starting products for the preparation of cephalosporins having a 3-carbomoyloxymethyl group (e.g. cefoxitin) by a well known process.

Even the recent WO 2004083217 operates through different steps with all the isolations which the previous literature describes, claiming inter alia certain halogenating agents already mentioned heretofore and the same isocyanates as those described in the literature.

SUMMARY OF THE INVENTION

It has now been surprisingly found possible to prepare acid cefoxitin of formula

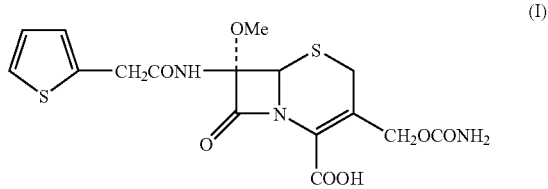

in a single step without any separation of intermediates and hence with yield and productivity advantages.

Such a process is characterised in that a compound of formula

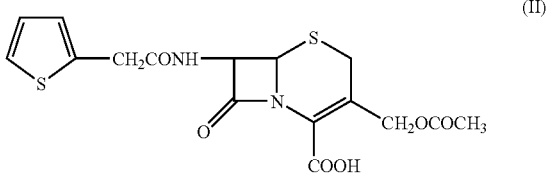

or a trimethylsilyl derivative thereof is dissolved in methylene chloride and then reacted at a temperature between −80° and −95° C. with at least one positive chlorine donor chosen from the group consisting of ethyl dichlorourethane and N-chlorosuccinimide, and with sodium methylate dissolved in methanol, to give a compound of formula

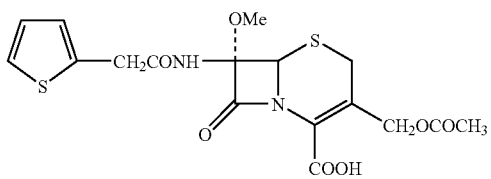

(IV)

which is then desacetylated with an aqueous sodium hydroxide solution to give a compound of formula

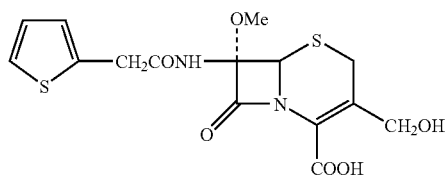

(V)

(v)
which is finally carbamoylated by reaction with chlorosulphonylisocyanate in tetrahydrofuran at a temperature between −45° and −50° C., to give the aforesaid compound of formula (I), which is isolated in acid form.

The acid cefoxitin of formula (I) obtained in this manner is then transformed into the corresponding sodium salt by treatment with the cationic resin Relite CNS of Resindion S.R.L., (Mitsubishi Chem. Corp.) in methanolic solution, within the temperature range between +10° and +25° C., to give a solution from which, after filtering off the resin, said sodium salt is crystallized.

DETAILED DESCRIPTION OF THE INVENTION

The following non-limiting examples illustrate the process of the present patent application.

EXAMPLE 1

Preparation of Acid Cefoxitin 200 g of sodium cefalotin are added to a mixture of 1600 ml of methylene chloride and 165 ml of methanol.

34 ml of methanesulphonic acid are added dropwise into the suspension cooled to −5° C., while maintaining the temperature at −5° C.

The mixture is stirred for 15 minutes while maintaining the temperature at 0°/−5° C., until a complete solution is obtained.

The solution is cooled to −85°/−90° C. and then 60.5 g of N-chlorosuccinimide are added.

A solution of sodium methylate, maintained at −10°/−15° C. and prepared by diluting 688.5 g of a 30 wt % methanolic solution of sodium methylate in 300 ml of methanol, is added dropwise over three hours while maintaining the reaction temperature at −85°/−87° C. The dropping funnel for the sodium methylate solution is washed with 13 ml of methanol.

30.2 g of N-chlorosuccinimide are added at −80° C. and the mixture stirred at −80° C. for one hour. A further 31.15 g of N-chlorosuccinimide are added at −80° C., stirring is maintained for two hours at −80° C., then 41.2 g of sodium metabisulphite are added. Stirring is continued for 5 minutes while maintaining the temperature at −78°/−80° C., then 302.7 g of 80% acetic acid are added.

A solution of 284 g of NaCl in 2360 ml of water is added and the pH adjusted to 2 with about 1000 ml of 1:1 HCl. The mixture is stirred for 10 minutes, the methylene phase is separated and the aqueous phase washed with 240 ml of methylene chloride. The methylene phases are pooled and washed with a solution of 106 g of NaCl in 1060 ml of water. The mixture is extracted at pH 7 with a solution of sodium bicarbonate in 320 ml of water. The aqueous phase is separated while the methylene phase is washed with 200 ml of water at pH 7. 680 ml of methanol are added to the pooled aqueous phases and cooled to −35°/−37° C.

A 30 wt % aqueous solution of 88.4 g of sodium hydroxide in 160 ml of water are added in 90 minutes while maintaining the temperature at −350/−37° C. The mixture is left to react for about 1 hour, until the substrate has reacted completely.

At the end of the reaction 48 ml of 80% acetic acid are added, raising the temperature to +10° C.

The pH is corrected to 6.5 with 80% acetic acid and the methanol eliminated by distillation under reduced pressure, at a temperature lower than +30° C. Sodium chloride is added to the residual aqueous solution until saturated. A solution of 138.2 g of tetrabutylammonium bromide in 540 ml of methylene chloride is added to the saturated sodium chloride solution, then stirring for 60 minutes at ambient temperature. The phases are separated and the aqueous phase re-extracted twice with a solution of 8.7 g of tetrabutylammonium bromide in 150 ml of methylene chloride. The resultant aqueous phase is extracted a further three times with methylene chloride, until complete extraction of the aqueous phase product.

The methylene phases are pooled and the solvent distilled off under reduced pressure at about 30° C., until an oily residue is obtained. This is taken up in three 300 ml of portions of anhydrous acetonitrile and again distilled under reduced pressure, each time until an oily residue is obtained. It is taken up in 500 ml of anhydrous tetrahydrofuran, distilled under reduced pressure until an oily residue is obtained, which is taken up in 500 ml of tetrahydrofuran, diluted to 1200 ml of with tetrahydrofuran, cooled to −50° C. and 80 g of chlorosulphonyl isocyanate poured in, maintaining the temperature at −45°/−50° C. The reaction mixture is transferred into a reactor containing 270 ml of water precooled to +5° C. and the temperature maintained at not greater than +10° C. The mixture is stirred for 2 hours at a temperature between 0° C. and +5° C.

750 ml of ethyl acetate are added, the organic phase is separated and washed three times with a solution of 190 g of NaCl in 1900 ml of water. The rich organic phase is extracted with a solution of 97.3 g of NaCl in 1300 ml of water, correcting the pH to 7 with sodium bicarbonate. The mixture is stirred for 10 minutes and the phases separated. The organic phase is extracted with 90 ml of a 10% NaCl solution.

The aqueous phase is added to the preceding and washed twice with 386 ml of ethyl acetate. The pH of the rich aqueous phase is corrected to 5.5 with 80% acetic acid, then 1.8 g of sodium hydrosulphite and 18.9 g of decolorizing carbon are added. The mixture is stirred for 30 minutes, filtered and the filter washed with 380 ml of water. The rich aqueous phase is acidified with 1:1 HCl to pH 2 and then cooled to +5° C. The precipitate is filtered off, washed with a mixture of 200 ml of water and 11.2 ethyl acetate.

The wet solid is dissolved in 500 ml of water and sodium bicarbonate added to pH 6.5-7.0, the solution is decolorized with carbon and sodium hydrosulphite and the filter is washed with 100 ml of water. 10% of ethyl acetate is added to the decolorized solution and the pH is corrected to 2 with 1:1 HCl.

It is left to crystallize at 5°/10° C., filtered, the product washed with 150 ml of water mixed with 10 ml of ethyl acetate, then dried under reduced pressure at 40°/45° C.

98 g of acid cefoxitin are obtained with a content of 94.4% "as such" (i.e. 98.6% on an anhydrous basis).

EXAMPLE 2

Preparation of Acid Cefoxitin 200 g of sodium cefalotin are suspended in 3330 ml of methylene chloride, 82.7 g of trimethylchlorosilane are added and the mixture stirred overnight at ambient temperature. It is cooled to −90° C. and 1216 g of a 30% solution of sodium methylate in methanol, diluted with 2320 ml of methanol and cooled to −15°/−20° C., are added dropwise in 75 minutes. The mixture is stirred at −90° C. for 60 minutes, cooled to −95° C. and 64 ml of ethyl dichlorourethane are added, stirring then being maintained for 90 minutes at −90° C. On termination of the reaction, 45.3 g of sodium metabisulphite are added and the mixture left to react for 5 minutes. 500 g of 80% acetic acid are added followed by a solution of 284 g of NaCl in 2360 ml of water, correcting the pH to 2 with about 1 liter of 1:1 HCl. The mixture is stirred for 10 minutes, the rich methylene phase is separated and the aqueous phase extracted with 240 ml of methylene chloride. The organic phases are pooled, washed three times with a solution of 106 g of NaCl in 1060 ml of water, then extracted at pH 7 with 320 ml of an aqueous sodium bicarbonate solution. The rich aqueous phase is separated, the methylene phase extracted with 200 ml of water at pH 7, the phases separated and the two rich phases pooled. The resultant aqueous phase is washed with 200 ml of methylene chloride, adding 680 ml of methanol to the aqueous phase after separation. The mixture is cooled to −35°/−37° C., and 88.4 g of a 30% sodium hydroxide solution diluted with 160 ml of water are added in about 90 minutes. On termination of the reaction, 48 ml of 80% acetic acid are added, the temperature raised to 10° C. and the pH corrected to 6.5 with 80% acetic acid. The mixture is distilled under reduced pressure at a temperature less than 30° C., until the methanol disappears. NaCl is added to the resultant aqueous solution until saturated, then a solution of 138.2 g of tetrabutylammonium bromide in 540 ml of methylene chloride is added and the mixture kept stirring for 60 minutes at ambient temperature. The phases are separated, the aqueous phase is extracted twice with 150 ml of methylene chloride containing 8.7 g of tetrabutylammonium bromide. The rich organic phase is separated.

The separated aqueous phase is extracted completely with methylene chloride 2-3 times and the methylene washes are added to the rich methylene phase. The organic phase is distilled at a temperature of about 30° C. under reduced pressure, until an oily residue is obtained. It is taken up three times with 300 ml of anhydrous acetonitrile, each time distilling under reduced pressure to obtain an oily residue, which is finally diluted with 500 ml of tetrahydrofuran. This is distilled under reduced pressure and the residue taken up in 500 ml of tetrahydrofuran. The volume is increased to 1200 ml with tetrahydrofuran, cooled to −50° C., and 80 g of chlorosulphonyl isocyanate are added, maintaining the temperature between −45° and −50° C. The reaction mixture is transferred into a reactor containing 270 ml of water precooled to 5° C., the temperature being maintained below +10° C. On termination of the reaction 750 ml of ethyl acetate are added, and the organic phase is washed three times with a solution of 190 g of NaCl in 1900 ml of water. To the rich organic solution an aqueous solution of 97.3 g of NaCl in 1300 ml of water is added, correcting the pH to 7 with sodium bicarbonate. The mixture is stirred, the phases separated, and the organic phase is again extracted with 190 ml of a 10% aqueous NaCl solution. After separation, the aqueous phases at pH 7 are pooled, the aqueous phase washed twice with 385 ml of ethyl acetate, the pH of the aqueous phase is corrected to 5.5 with 80% acetic acid, then 1.8 g of sodium hydrosulphite and 18.9 g of decolorizing carbon are added. The mixture is stirred for 30 minutes, filtered and the filter washed with 380 ml of water. 245 ml of ethyl acetate are added to the rich aqueous phase and the pH is corrected to 2 with 1:1 HCl. The mixture is cooled to +5° C., left to crystallize for 60 minutes, filtered and the product washed with a mixture of 200 ml of water and 11.2 ethyl acetate.

The wet product is suspended in 500 ml of water and then dissolved by adding sodium bicarbonate until pH 6.5-7.0. The solution is decolorized with carbon and sodium hydrosulphite and the filter is washed with 100 ml of water, 90% ethyl acetate is added, and the pH is corrected at 5°/10° C. to 2 with 1:1 HCl. The product is filtered off, washed with 150 ml of water mixed with 10 ml of ethyl acetate, then dried under reduced pressure at 40°/45° C. Yield 96 g with a content of 94.1% (i.e. 98.3% on an anhydrous basis).

EXAMPLE 3

Preparation of Cefoxitin Sodium Salt 70 g of acid cefoxitin are dissolved in anhydrous methanol at 18°/22° C., cooled to 14°/16° C. and 150 g of Relite CNS (sodium salt) added at 14°/16° C.

The mixture is stirred for 90 minutes at 14°/16° C, then water added until a clear supernatant solution appears while the resin deposits as a bottom layer in the reactor. The liquid is filtered off, washed firstly with a mixture of 50 ml methanol +30 ml acetone, then with a mixture of 75 ml methanol +50 ml acetone.

It is decolorized with 2.8 g carbon for 20 minutes at 14°/16° C., filtered, the filter washed with a mixture of 25 ml methanol +25 ml acetone and again with the same mixture. 350 ml acetone are added over 15 minutes while maintaining the temperature at 14°/16° C. A sterile sodium cefoxitin seed (75-100 mg) is added while maintaining stirring at 14°/16° C., then 1800 ml acetone are added over 3 hours. Stirring is again applied for 30 minutes at 14°/16° C., then the crystalline solid is filtered off. The filter is washed twice with a mixture of 120 ml acetone +30 ml methanol, then with 75 ml acetone and finally with 125 ml acetone.

The product is dried in an oven at 60° C. under reduced pressure.

Yield: 60 g of white crystalline product, free of anionic residues of 2-ethylhexanoate type, acetate and the like.

Content: 98.8% as anhydrous sodium salt, free of solvents.

What we claims is:

1. A process for preparing acid cefoxitin of formula (I)

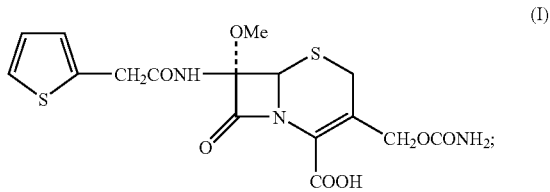

wherein:
(A) a compound of formula (II)

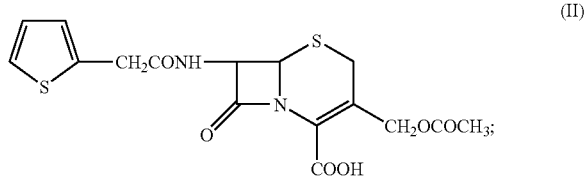

or a trimethylsilyl derivative thereof is dissolved in methylene chloride and then reacted at a temperature between −80° and −95° C. with at least one positive chlorine donor selected from the group consisting of ethyl dichlorourethane and N-chloro-succinimide, and with sodium methylate dissolved in methanol, to give a compound of formula (IV)

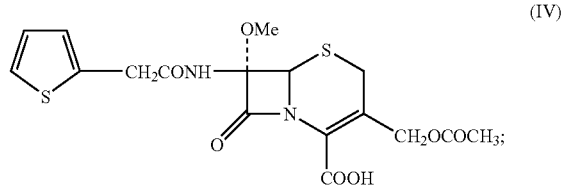

(B) the compound of formula (IV) is desacetylated with an aqueous sodium hydroxide solution to give a compound of formula (V)

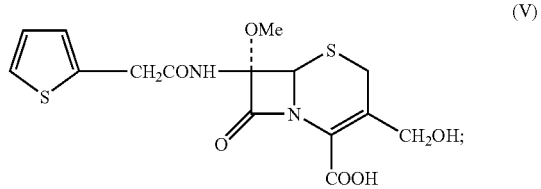

and finally
(C) the compound of formula (V) is carbamoylated by reaction with chlorosulphonylisocyanate in tetrahydrofuran at a temperature between −45° and −50° C., to give the aforesaid acid cefoxitin of formula (I), which is isolated in acid form; and wherein said process of preparing acid cefoxitin of formula (I) is carried out without any separation of intermediates.

2. A process as claimed in 1, wherein the positive chlorine donor is ethyl dichlorourethane.

3. A process as claimed in claim 1, wherein the positive chlorine donor is N-chlorosuccinimide.

4. A process for preparing acid cefoxitin of formula (I)

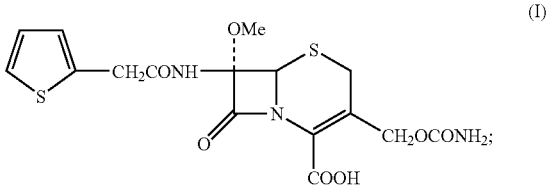

wherein:
(A) a compound of formula (II)

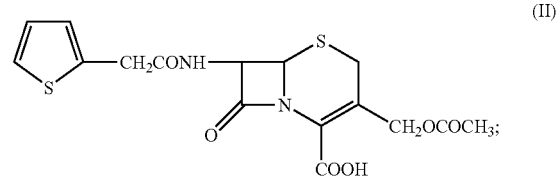

or a trimethylsilyl derivative thereof is dissolved in methylene chloride and then reacted at a temperature between −80° and −95° C. with at least one positive chlorine donor selected from the group consisting of ethyl dichlorourethane and N-chloro-succinimide, and with sodium methylate dissolved in methanol, to give a compound of formula (IV)

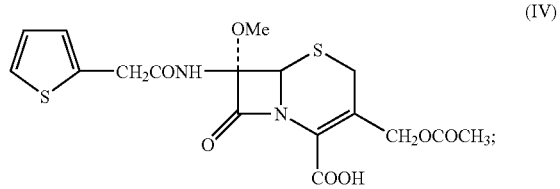

(B) the compound of formula (IV) is desacetylated with an aqueous sodium hydroxide solution to give a compound of formula (V)

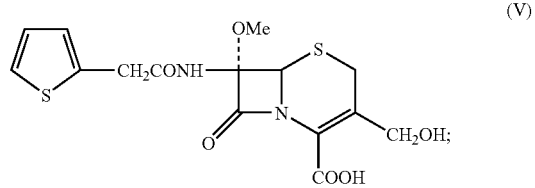

and finally
(C) the compound of formula (V) is carbamoylated by reaction with chlorosulphonylisocyanate in tetrahydrofuran at a temperature between −45° and −50° C., to give the aforesaid acid cefoxitin of formula (I), which is isolated in acid form; whereby acid cefoxitin of formula (I) is prepared without isolation of intermediates.

5. A process as claimed in claim 4, wherein the positive chlorine donor is ethyl dichlorourethane.

6. A process as claimed in claim 4, wherein the positive chlorine donor is N-chlorosuccinimide.

* * * * *